(12) United States Patent
Navon

(10) Patent No.: US 8,017,407 B2
(45) Date of Patent: Sep. 13, 2011

(54) DEVICE AND METHOD FOR MONITORING BLOOD PARAMETERS

(76) Inventor: Ariel Navon, Hod HaSharon (IL)

( * ) Notice: Subject to any disclaimer, the term of this patent is extended or adjusted under 35 U.S.C. 154(b) by 67 days.

(21) Appl. No.: 12/593,246

(22) PCT Filed: Mar. 26, 2008

(86) PCT No.: PCT/IL2008/000413
§ 371 (c)(1),
(2), (4) Date: Sep. 25, 2009

(87) PCT Pub. No.: WO2008/117286
PCT Pub. Date: Oct. 2, 2008

(65) Prior Publication Data
US 2010/0076281 A1    Mar. 25, 2010

Related U.S. Application Data

(60) Provisional application No. 60/920,116, filed on Mar. 27, 2007.

(51) Int. Cl.
*G01N 21/00* (2006.01)

(52) U.S. Cl. ............ 436/164; 436/70; 436/171; 60/322; 60/323; 60/324; 60/334; 60/335

(58) Field of Classification Search .................. None
See application file for complete search history.

(56) References Cited

U.S. PATENT DOCUMENTS

| | | | |
|---|---|---|---|
| 4,142,101 A | 2/1979 | Yin | |
| 6,213,952 B1 | 4/2001 | Finarov et al. | |
| 6,522,911 B1 | 2/2003 | Toida et al. | |
| 6,587,704 B1 | 7/2003 | Fine et al. | |
| 6,660,995 B1 | 12/2003 | Canpolat et al. | |
| 6,662,031 B1 | 12/2003 | Khalil et al. | |
| 6,671,528 B2 | 12/2003 | Steuer et al. | |
| 6,681,128 B2 | 1/2004 | Steuer et al. | |
| 6,873,865 B2 | 3/2005 | Steuer et al. | |
| 2006/0247506 A1 | 11/2006 | Balberg et al. | |
| 2007/0038041 A1 | 2/2007 | Yang et al. | |

OTHER PUBLICATIONS

Dam et al. "Fiber-optic probe for noninvasive real-time determination of tissue optical properties at multiple wavelengths." *Applied Optics*, vol. 40, issue 76, pp. 1155-1164 Abstract Only.

Kienle et al. "Spatially resolved absolute diffuse reflectance measurements for noninvasive determination of the optical scattering and absorption coefficients of biological tissue." *Applied Optics*, vol. 35, Issue 13, pp. 2304-2314. Abstract Only. Wang et al., "Source of error in calculation of optical diffuse reflectance from turbid media using diffusion theory," (2000), pp. 163-170.

Kienle et al., "Spatially resolved absolute diffuse reflectance measurements for noninvasive determination of the optical scattering and absorption coefficients of biological tissue," (1996), pp. 2304-2313.

Lin et al., "Measurement of tissue optical properties by the use of oblique-incidence optical fiber reflectometry," (1997), pp. 136-143.

*Primary Examiner* — Yelena G Gakh
*Assistant Examiner* — Robert Xu
(74) *Attorney, Agent, or Firm* — Merchant & Gould P.C.

(57) ABSTRACT

A device and method measuring at least one parameter related to the blood of a subject, by emitting light with at least one emitter at least one wavelength within the spectral range of 380 980 nm toward a body part containing at least one wavelength. Spatially resolved reflectance measurements are obtained by capturing light reflected by the body part with at least one reflectance detector. At least one of the absorption coefficient and the reduced scattering coefficient of the blood component of the body part at each of the wavelengths is extracted from the measurements. The temporal derivatives of the at least one of the absorption coefficient and the reduced scattering coefficient is extracted, and at least one blood related parameter is calculated using the temporal derivatives.

12 Claims, 6 Drawing Sheets

DEVICE AND METHOD FOR MONITORING BLOOD PARAMETERS

FIELD OF THE DISCLOSED TECHNIQUE

This application is a National Stage Application of PCT/IL2008/000413, filed Mar. 26, 2008, which claims benefit of Ser. No. 60/920,116, filed Mar. 27, 2007 in the United States of America and which applications are incorporated herein by reference. To the extent appropriate, a claim of priority is made to each of the above disclosed applications.

The disclosed technique relates to non-invasive methods for continuous monitoring of the blood parameters of a subject.

BACKGROUND OF THE DISCLOSED TECHNIQUE

The term "hematocrit" (Hct) refers to the proportion of a blood volume occupied by red blood cells (RBCs). The RBCs contain hemoglobin (approximately 34% by volume), which enables the delivery of oxygen from the lungs to the various tissues in the body. The normal ranges of hematocrit for an individual varies with age and gender, but is generally around 42-54% for adult men and 38-46% for adult women. The hematocrit measurement of a patient is useful for various medical diagnoses. A low hematocrit usually indicates anemia (a deficiency in RBCs and hemoglobin). Anemia may result from acute blood loss (e.g., traumatic injury, surgery, colon cancer), nutritional deficiency (e.g., iron, folic acid, vitamin B-12), or various other clinical factors (e.g., cancer, medication effects, hereditary disorders, etc). An elevated hematocrit may be due to dehydration, or may indicate other conditions, such as a myeloproliferative disorder (type of bone marrow disorder) or chronic obstructive pulmonary disease and other conditions associated with hypoxia (oxygen deficiency in the body).

The hematocrit is usually measured with invasive techniques. In one common technique, blood is drawn from the patient, and then a high speed centrifuge is used to separate the different blood components into separate layers inside a capillary tube. The relative height of the RBC layer in the tube is measured relative to the total blood volume, to provide the hematocrit value. The drawn blood may also be analyzed by other methods, such as by taking optical measurements of the blood. The hematocrit value may be calculated using an automated instrument, as part of a complete set of blood tests.

The aforementioned invasive measurement involves inconvenience and discomfort for the subject, and also introduces the risk of contamination to both the subject and the medical staff performing the measurement. Additionally, any invasive method (such as the centrifuging technique) entails a delay between when the blood sample is drawn and when the hematocrit value is obtained. Moreover, the determination of hematocrit (as well as other types of blood tests) is usually based on individual measurements. In certain situations, it is beneficial to perform continuous monitoring of the hematocrit of a subject, to effectively diagnose and treat certain serious or life-threatening medical conditions (e.g., during intensive care, or when performing surgery). However, if an invasive measurement technique is being used, it is not possible to obtain immediate results, nor can continuous real-time tracking of the hematocrit of the subject be performed.

Pulse oximetry is a non-invasive method for measuring the level of oxygen saturation in the hemoglobin of a patient. A hemoglobin molecule bounded with oxygen is known as oxy-hemoglobin ($HbO_2$) and a hemoglobin molecule without bound oxygen is known as deoxyhemoglobin (Hb). Pulse oximetry involves emitting light at two or more separate wavelengths (e.g., red and infrared light) across a body part, such as a fingertip. The total attenuation of each of the two wavelengths is measured using sensors (i.e., based on reflectance or transmittance measurements). Pulse oximetry utilizes the pulsing nature of the blood vessels, in order to isolate the blood in the artery from other tissues which the light passes through (e.g., skin, bone, muscle, fat, fingernail, etc). The various blood vessels in the body change volume in a cyclic manner, due to the pumping action of the heart as the blood circulates throughout the body. The ratio between oxyhemoglobin and deoxyhemoglobin components in the blood is determined based on the different absorption spectra of oxyhemoglobin and deoxyhemoglobin. It is noted that pulse oximetry only reveals the percentage of oxygen saturation in the hemoglobin (i.e., the percentage of oxyhemoglobin relative to deoxyhemoglobin), and provides no information regarding other blood parameters, such as the total oxygen content in the blood, the amount of oxygen dissolved in the blood, or the absolute hematocrit value. Therefore, pulse oximetry cannot be used to diagnose various disorders, such as anemia or states of elevated hematocrit (for instance, the existing RBCs may be fully oxygenated, but there may not be sufficient blood cells).

Contemporary approaches for the noninvasive measurement of blood parameters such as hematocrit are usually based on the concept implemented in pulse oximetry of isolating the blood from the other tissues, by analyzing the total attenuation of light passing through the body part of the subject due to the blood in the body tissue. However, even after isolating the blood component, the total light attenuation is a function of at least two unknown parameters: the total blood volume and the hematocrit value, which are each independent absolute values (unlike the ratio measurement which provides the hemoglobin oxygenation). Therefore, an additional measurement is required in order to be able to determine both parameters. For example, an additional measurement relating to the total amount of blood can be carried out to extract its relationship to the total attenuation, and thereby solve for the hematocrit value.

Other methods that aim to isolate the blood from other tissues are based on physiological properties of RBCs in certain conditions, such as occlusion, in which cessation of blood flow is established at the measurement location (e.g., by applying over-systolic pressure at a location upstream of the measurement location with respect to the direction of normal blood flow). Such methods are described in U.S. Pat. No. 6,213,952 to Finarov et al, entitled "Optical device for non-invasive measurement of blood related signals using a finger holder", and U.S. Pat. No. 6,587,704 to Fine et al, entitled "Method for non-invasive optical measurements of blood parameters".

U.S. Pat. No. 6,662,031 to Khalil et al, entitled "Method and device for the noninvasive determination of hemoglobin and hematocrit", discloses the determination of the hemoglobin concentration and hematocrit value of a human tissue sample based on steady state reflectance measurements, and the localized control of the temperature of the tissue sample. The body part is set to a particular temperature within a physiological temperature range (below the core temperature of the body), and the skin surface is illuminated by light at wavelengths within the spectral range of about 400 nm to about 900 nm. Detectors positioned at particular separation distances collect the reflect light (e.g., using spatially resolved diffuse reflectance measurement techniques), while the temperature is being maintained. A second set of measurements are acquired while the body part is set to another temperature. Optical parameters are determined at each temperature, along with the temperature dependence of the optical parameters. The hemoglobin concentration or the hematocrit value is determined based on a calibration relationship that relates the optical parameters at a given temperature, and the dependence of the optical parameters on temperature with the hemoglobin concentration or hematocrit value.

U.S. Pat. No. 6,671,528, and the continuation U.S. Pat. No. 6,873,865 to Steuer et al, both entitled "Method and apparatus for non-invasive blood constituent monitoring", describe the determination of blood hematocrit in a living tissue based on an attenuation measurement and an energy measurement. Radiation at a selected wavelength is directed toward a body part, and detectors obtain transmittance or reflectance measurements. An energy-detecting means (e.g., a pressure transducer) measures the temporal rate of change of the fractional blood volume (using one of several possible techniques). The hematocrit value is calculated from the attenuation measurements (from the detectors) and the energy measurements (from the energy-detecting means).

U.S. Pat. No. 6,681,128 to Steuer et al, entitled "System for noninvasive hematocrit monitoring", is directed to a method and system for noninvasive determination of the hematocrit and other blood parameters of a subject. The method involves passing at least two wavelengths through a body tissue and detecting the transillumination. The selected wavelengths are preferably at isosbestic points of reduced hemoglobin and oxyhemoglobin, to eliminate the effects of variable blood oxygenation. The hematocrit is calculated based on a ratio of extinction coefficients, in terms of the pulsatile component and the steady state component for each wavelength that is extinguished after passing through the body tissue.

SUMMARY OF THE DISCLOSED TECHNIQUE

In accordance with the disclosed technique, there is thus provided a method for measuring at least one parameter related to the blood of a subject. The method includes the procedure of emitting light with an emitter, at least one wavelength within the spectral range of 380-980 nm, toward a body part containing at least one blood vessel. The method further includes the procedure of obtaining spatially resolved reflection measurements, by capturing light reflected by the body part, with at least one reflectance detector. The method further includes the optional procedure of obtaining diffuse transmittance measurements, by capturing light passing through the body part, with at least one transmittance detector. The method further includes the procedures of extracting from the measurements at least one of: the absorption coefficient ($\mu_a$) and the reduced scattering coefficient ($\mu'_s$) of the blood component of the body part at each of the at least one wavelength, extracting the temporal derivatives of the at least one of the absorption coefficient and the reduced scattering coefficient $$\left(\frac{\partial \mu'_s}{\partial t} \text{ and } \frac{\partial \mu_a}{\partial t}\right),$$

and calculating at least one blood parameter using the temporal derivatives. According to one embodiment of the disclosed technique, the hematocrit value of the subject is monitored, using light emitted at a single isosbestic wavelength for oxyhemoglobin and deoxyhemoglobin, such as at approximately 803 nm.

In accordance with the disclosed technique, there is further provided a device for measuring at least one parameter related to the blood of a subject. The device includes at least one emitter, at least one reflectance detector, and a processor. The emitter emits light at least one wavelength within the spectral range of 380-980 nm, toward a body part containing at least one blood vessel. The reflectance detectors obtain spatially resolved reflectance measurements, by capturing light reflected by the body part. The processor extracts at least one of: the absorption coefficient ($\mu_a$) and the reduced scattering coefficient ($\lambda'_s$) of the blood component of the body part at each of the at least one wavelength, extracts the temporal derivatives of the at least one of the absorption coefficient and the reduced scattering coefficient $$\left(\frac{\partial \mu'_s}{\partial t} \text{ and } \frac{\partial \mu_a}{\partial t}\right),$$

and calculates at least one blood related parameter using the temporal derivatives. The device may further include at least one transmittance detector, for obtaining diffuse transmittance measurements by capturing light passing through the body part.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

Figure 1:
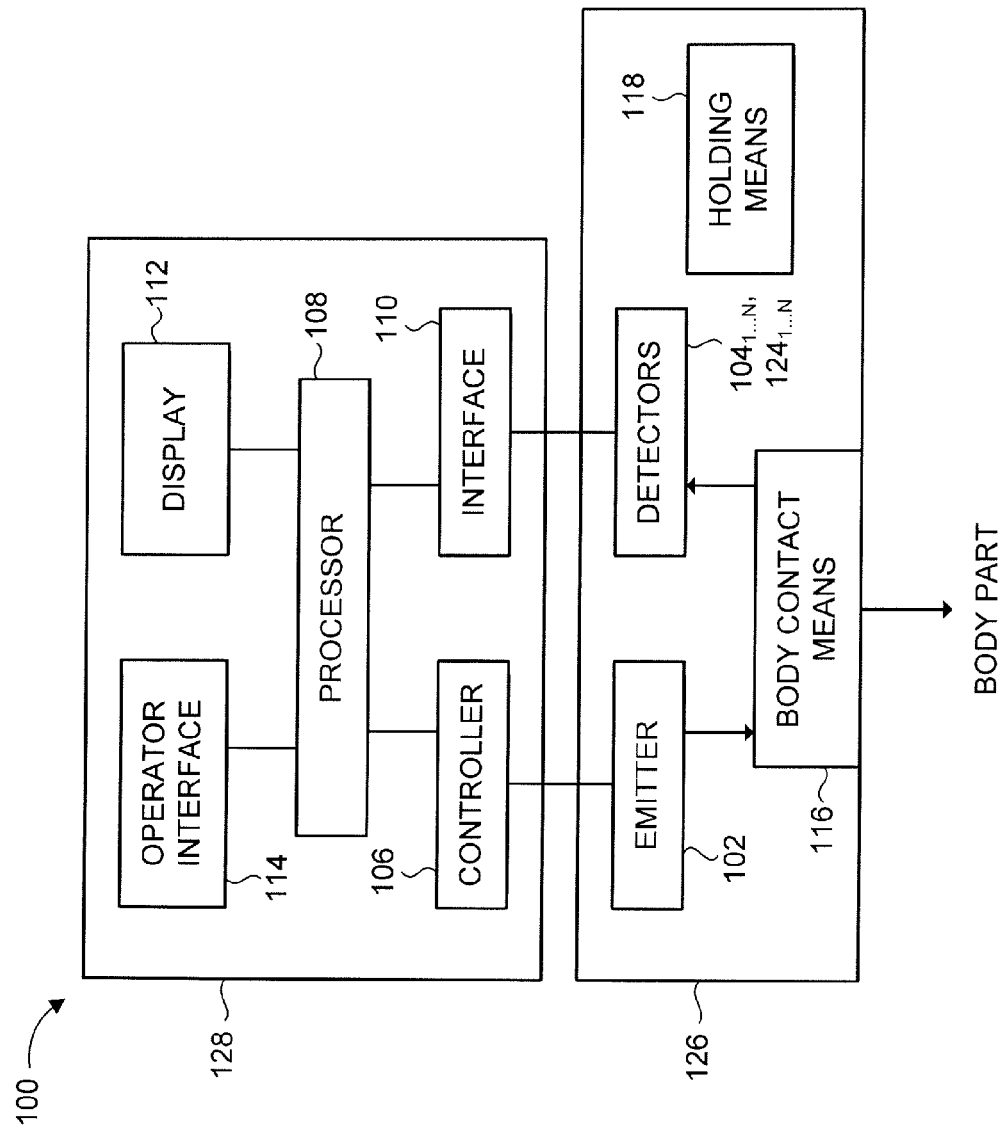
FIG. 1 is a schematic illustration of a device for monitoring the hematocrit of a subject, constructed and operative in accordance with an embodiment of the disclosed technique.

The disclosed technique overcomes the disadvantages of the prior art by providing a device and method for non-invasive continuous monitoring of blood related parameters of a subject, such as the hematocrit value (Hct). The method is essentially analytic (i.e., does not rely on calibration), and is based on simple optical measurements. The method utilizes the temporal changes in the optical properties of different tissue components in the inspected body tissue. The method provides hematocrit measurement using a single optical transmission at a single wavelength, by isolating the optical parameters of the blood component from those of other tissue components. According to one embodiment of the disclosed technique, an emitter emits light at an isosbestic wavelength for oxyhemoglobin and deoxyhemoglobin toward a body part, such as a finger. Detectors acquire spatially resolved reflectance measurements, and optical parameters of the inspected body tissue are extracted from these measurements. Optionally, diffuse transmittance measurements may be carried out in addition to the reflectance measurements, for further validation and increased accuracy. The hematocrit value is calculated based on an equation which relates the ratio of the temporal derivatives of the inspected body part to the hematocrit, where the equation is valid at the isosbestic wavelength.

Biological tissue is a turbid medium, meaning that it both scatters and absorbs light. The propagation of light through a biological tissue can be described by the radiative transfer equation (RTE). The diffusion approximation to the RTE provides an expression in terms of three optical parameters: the absorption coefficient ($\mu_a$), the scattering coefficient ($\mu_s$), and the scattering phase function. The phase function is represented by the anisotropy parameter $g=\langle\cos\theta\rangle$, which is the average cosine of the scattering angle. Using the similarity principle, the scattering coefficient ($\mu_s$) and the anisotropy parameter (g) may be combined into a single transport scattering coefficient $\mu_s'=\mu_s(1-g)$, herein referred to as the "reduced scattering coefficient". Accordingly, the propagation of light through a biological tissue can be expressed in terms of two optical parameters: the absorption coefficient ($\mu_a$) and the reduced scattering coefficient ($\mu_s'$) of the tissue. Typical coefficient values for soft tissues are: $\mu_a \approx 0.0\text{-}10 \text{ cm}^{-1}$ and $\mu_s' \approx 10\text{-}100 \text{ cm}^{-1}$.

With regard to the Beer-Lambert Law, the total absorption of light through a biological tissue sample may be treated as a weighted combination of the absorption of its constituent elements. In particular, the total absorption is equivalent to the sum of the individual absorption coefficients of each element, weighted by their relative concentrations:

$$\mu_a = \mu_{a,blood} \cdot C_b + \mu_{a,water} \cdot C_w + \mu_{a,rest} \cdot C_{rest} \quad (1)$$

where:

$\mu_{a,blood}$=absorption coefficient for the whole blood component in the tissue sample;

$\mu_{a,water}$=absorption coefficient for the water in the tissue sample (not including the water in the blood);

$\mu_{a,rest}$=absorption coefficient for all components in the tissue sample other than water and blood (e.g., skin, bone);

$C_b$=volumetric percentage of blood in the total tissue sample;

$C_w$=volumetric percentage of water in the total tissue sample (not including the water in the blood); and $C_{rest}$=volumetric percentage of all components in the total tissue sample other than water and blood.

The total reduced scattering coefficient of the tissue sample can be derived in a similar manner according to the relative concentrations of the scattering components in the tissue (the scattering due to water is negligible):

$$\mu_s' = \mu_{s,blood}' \cdot C_b + \mu_{s,rest}' \cdot C_{rest} \quad (2)$$

where:

$\mu_{s,blood}'$=reduced scattering coefficient for the whole blood component in the tissue sample; and $\mu_{s,rest}'$=reduced scattering coefficient for all components in the tissue sample other than water and blood.

The absorption coefficient for the whole blood component ($\mu_{a,blood}$) may be expressed as a weighted combination of the individual absorption components in the blood, as follows:

$$\mu_{a,blood} = \frac{0.34 Hct}{V}(\sigma_{ox} SAT + (1-SAT)\sigma_{deox}) + (1 - 0.34 Hct)\mu_{a,plasma}' \quad (3)$$

where:

Hct=hematocrit value (volumetric percentage of RBCs in the blood);

V=average volume of RBC;

SAT=fraction of blood oxygen saturation (amount of oxygenated RBCs in relation to total RBCs);

$\sigma_{ox}$=the absorption cross-section of oxygenated RBCs;

$\sigma_{deox}$=the absorption cross-section of deoxygenated RBCs; and $\mu_{a,plasma}'$=absorption coefficient for the plasma in the blood. For simplification purposes, this parameter includes the absorption due to all components in the blood other than the RBCs.

The absorption cross-section of the oxygenated and deoxygenated RBCs ($\sigma_{ox}$ and $\sigma_{deox}$) is related to the ability of a particle to scatter light, and is dependent on various characteristics of a single RBC (e.g., size, shape, complex refractive index, etc). These parameters can be calculated using Mie theory, and can be easily obtained from available publications.

The individual absorption coefficients may generally be expressed as: $\mu = \rho \cdot \sigma$, where $\rho$ represents the number density in the medium for that component (i.e., the component volume portion of the whole medium volume), and $\sigma$ represents the absorption cross-section of that component. For example, the following approximate relationship is applicable for oxygenated hemoglobin:

$$\rho = \frac{0.34 Hct \cdot SAT}{V}.$$

The reduced scattering coefficient for the whole blood component ($\mu_{s,blood}'$) is related to the hematocrit value according to the following exemplary equation (experimentally determined):

$$\mu_{s,blood}' = \frac{\sigma_{scat} Hct(1-Hct)(1.4-Hct)}{V} \quad (4)$$

where:

$\sigma_{scat}$=the transport scattering cross-section of RBCs.

Differentiating equations (1) and (2), respectively, with respect to time, results in:

$$\frac{\partial \mu_a}{\partial t} = \mu_{a,blood} \cdot \frac{\partial C_b}{\partial t} + \mu_{a,water} \cdot \frac{\partial C_w}{\partial t} + \mu_{a,rest} \cdot \frac{\partial C_{rest}}{\partial t} \quad (5)$$

and:

$$\frac{\partial \mu_s'}{\partial t} = \mu_{s,blood}' \cdot \frac{\partial C_b}{\partial t} + \mu_{s,rest}' \cdot \frac{\partial C_{rest}}{\partial t} \quad (6)$$

The temporal change of the volumetric percentage of each tissue component is due to the pulsing nature of the blood flow within the tissue. The various blood vessels in the body change volume in a cyclic manner, due to the pumping action of the heart as the blood circulates throughout the body. Thus, the time derivative of the volumetric percentage of blood in the tissue sample $$\left(\frac{\partial C_b}{\partial t}\right)$$

is the temporal change in the relative concentration of blood due to the pulsing blood flow.

The temporal variation of the blood component is much greater than the temporal variation of the other tissue components $$\left(\text{i.e., } \frac{\partial C_b}{\partial t} \gg \frac{\partial C_w}{\partial t}, \frac{\partial C_{rest}}{\partial t}\right).$$

At a spectral range where the absorption of blood is not significantly lower than the absorption of the other tissue components (i.e., where: $\mu_{a,blood} \ll \mu_{a,water}$, $\mu_{a,rest}$ does not hold), such as within the range of approximately 380-980 nm, equation (5) can be simplified to:

$$\frac{\partial \mu_a}{\partial t} \cong \mu_{a,blood} \cdot \frac{\partial C_b}{\partial t} \qquad (7)$$

From similar considerations, $$\mu'_{s,blood} \cdot \frac{\partial C_b}{\partial t} \gg \mu'_{s,rest} \cdot \frac{\partial C_{rest}}{\partial t},$$

and so equation (6) can be simplified to:

$$\frac{\partial \mu'_s}{\partial t} \cong \mu'_{s,blood} \cdot \frac{\partial C_b}{\partial t} \qquad (8)$$

At an isosbestic wavelength for oxyhemoglobin and deoxyhemoglobin, the absorbance of oxyhemoglobin and deoxyhemoglobin is equal (i.e., the absorption spectra for oxyhemoglobin and deoxyhemoglobin intersect at an isosbestic point), so that $\sigma_{abs} = \sigma_{ox} = \sigma_{deox}$. The wavelength of approximately 803 nm is one such isosbestic wavelength. In the spectral range of approximately 380-980 nm, the light absorption is primarily due to the hemoglobin of the RBCs, and so: $\mu_{a,blood} \gg \mu_{a,plasma}$. Therefore, at an isosbestic wavelength, equation (3) can be simplified to:

$$\mu_{a,blood} = \frac{Hct}{V}\sigma_{abs} \qquad (9)$$

(where the 0.34 factor in equation (3) is incorporated into $\sigma_{abs}$: i.e., $\sigma_{abs} = 0.34\sigma_{ox} = 0.34\sigma_{deox}$).

Equations (7) and (8) can be combined to yield:

$$\frac{\mu'_{s,blood}}{\mu_{a,blood}} = \frac{\frac{\partial \mu'_s}{\partial t}}{\frac{\partial \mu_a}{\partial t}} \qquad (10)$$

Substituting equations (4) and (9) into equation (10) results in:

$$\boxed{\frac{\frac{\partial \mu'_s}{\partial t}}{\frac{\partial \mu_a}{\partial t}} = \frac{\sigma_{scat}(1 - Hct)(1.4 - Hct)}{\sigma_{abs}}} \qquad (11)$$

Equation (11) relates the temporal rate of change of the reduced scattering coefficient in the blood component of the tissue sample $$\left(\frac{\partial \mu'_s}{\partial t}\right)$$

and the temporal rate of change of the absorption coefficient in the blood component of the tissue sample $$\left(\frac{\partial \mu_a}{\partial t}\right)$$

to the hematocrit value (Hct) of the tissue sample. The disclosed technique involves measuring these two variables with simple optical measurements, and then solving for the Hct value using equation (11). Alternatively, other equivalent equations which relate the variables of $$\left(\frac{\partial \mu_a}{\partial t}\right) \text{ and } \left(\frac{\partial \mu'_s}{\partial t}\right)$$

to the hematocrit value (Hct) may be used.

Figure 2:
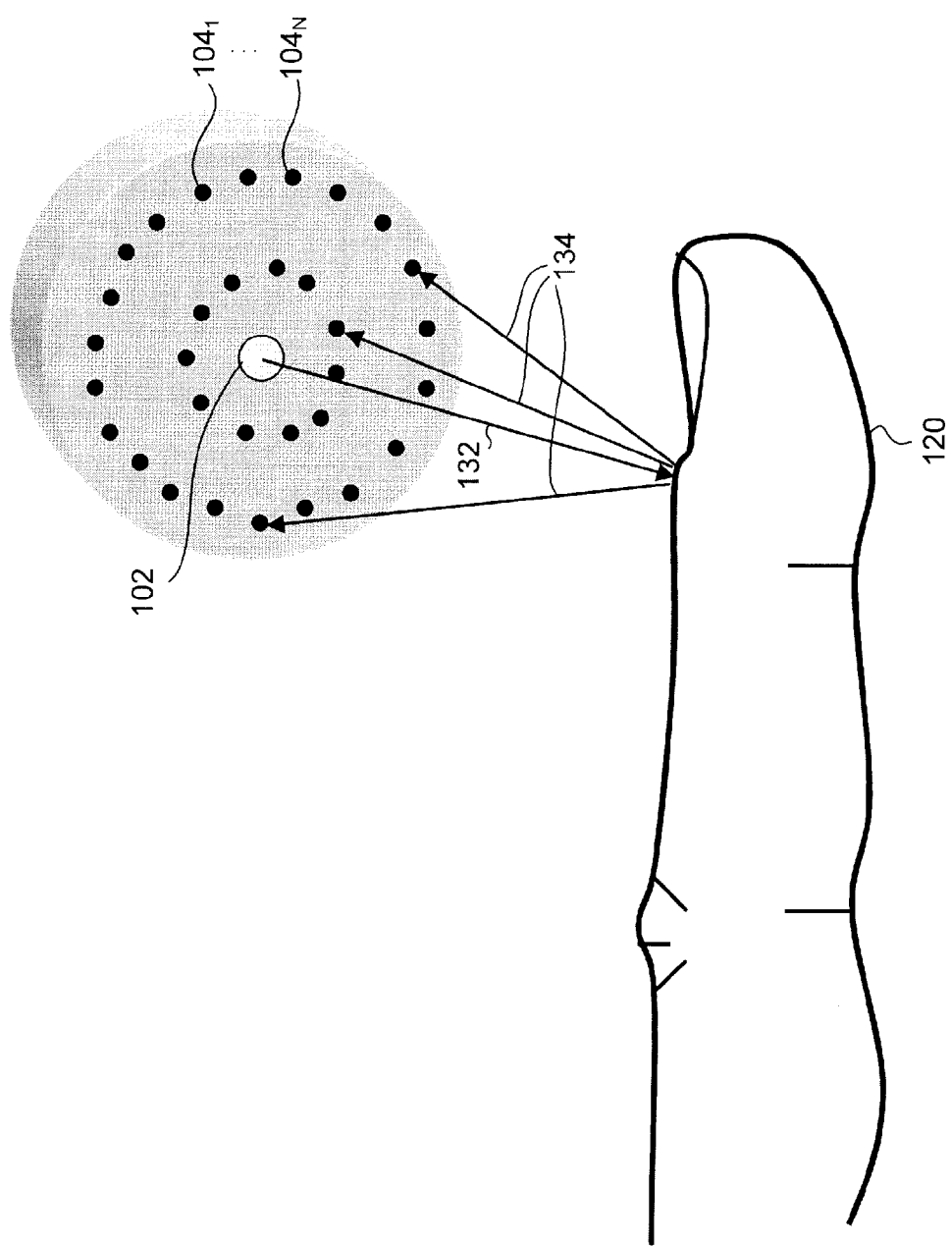
FIG. 2 is a schematic illustration of the device of FIG. 1 in operation.

Reference is now made to FIGS. 1 and 2. FIG. 1 is a schematic illustration of a device, generally referenced 100, for monitoring the hematocrit of a subject, constructed and operative in accordance with an embodiment of the disclosed technique. FIG. 2 is a schematic illustration of the device of FIG. 1 in operation. Device 100 includes an emitter 102, a plurality of reflectance detectors $104_1 \ldots 104_N$, a plurality of transmittance detectors $124_1 \ldots 124_N$, a controller 106, a processor 108, an interface 110, a display 112, an operator interface 114, a body contact means 116 and a holding means 118. Controller 106 is coupled with emitter 102, and with processor 108. Interface 110 is coupled with detectors $104_1 \ldots 104_N$ and detectors $124_1 \ldots 124_N$ and with processor 108. Processor 108 is further coupled with display 112 and with operator interface 114.

Device 100 includes a sensor module 126 coupled with a controller module 128. Sensor module 126 includes emitter 102, reflectance detectors $104_1 \ldots 104_N$, transmittance detectors $124_1 \ldots 124_N$, body contact means 116, and holding means 118. Controller module 128 includes controller 106, processor 108, interface 110, display 112, and operator interface 114. Although sensor module 126 and controller module 128 are typically separate and distinct units (i.e., each enclosed in separate housings), it is appreciated that this represents an exemplary implementation of device 100, and that the various components of device 100 may be organized differently.

Emitter 102 emits radiation toward a body part 120 of the subject. Body part 120 is depicted in FIG. 2 as a finger, but it is appreciated that the body part may be another region in the body which is easily accessible and convenient for the medical staff to apply the emitted light. For example, body part 120 may also be the: toe, outer ear, eardrum, earlobe, mouth, eye, other regions of the hand (e.g., the palm, the webbing between the fingers), and the like. Emitter 102 may be a light emitting diode (LED), or another type of light emitting element. Emitter 102 may direct the light to body part 120 through an optical element, such as a waveguide or an optical fiber.

Figure 3:
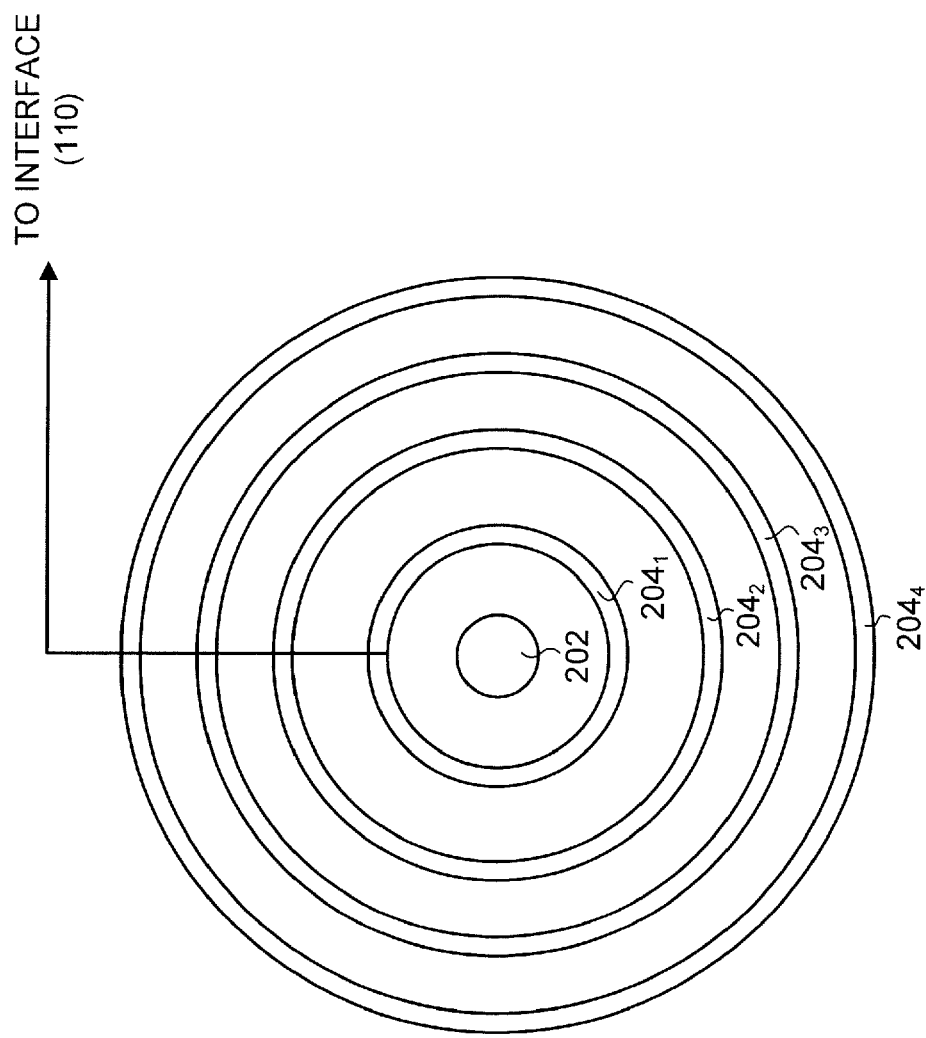
FIG. 3 is a schematic illustration of a continuous reflectance detector arrangement, constructed and operative in accordance with another embodiment of the disclosed technique.

Reflectance detectors $104_1 \ldots 104_N$ are arranged at varying distances with respect to the optical axis of emitter 102. Detectors $104_1 \ldots 104_N$ may be arranged in a radial pattern surrounding emitter 102, and integrated a single unit together with emitter 102 (as depicted in FIG. 2). Reflectance detectors $104_1 \ldots 104_N$ detect light reflected from body part 120, in accordance with a spatially resolved reflectance measurement technique (elaborated upon herein below). Reflectance detectors $104_1 \ldots 104_N$ and transmittance detectors $124_1 \ldots 124_N$ detect light at the operational wavelength range (i.e., between approximately 380-980 nm). Reflectance detectors $104_1 \ldots 104_N$ and transmittance detectors $124_1 \ldots 124_N$ may be operative to detect light only at the desired wavelength (i.e., a narrow band sensor). Optionally, a bandpass filter may be used to block light outside the desired wavelength from reaching reflectance detectors $104_1 \ldots 104_N$ or transmittance detectors $124_1 \ldots 124_N$. Reflectance detectors $104_1 \ldots 104_N$ and transmittance detectors $124_1 \ldots 124_N$ may be photodiodes, or other types of light detection elements. Reflectance detectors $104_1 \ldots 104_N$ may be arranged as a series of discrete light detection elements, as depicted in FIG. 2, or as a continuous array of light detection elements. Reference is made to FIG. 3, which is a schematic illustration of a continuous reflectance detector arrangement, constructed and operative in accordance with another embodiment of the disclosed technique. Reflectance detectors $204_1 \ldots 204_N$ are analogous to reflectance detectors $104_1 \ldots 104_N$ of FIG. 2, apart from the fact that each of reflectance detectors $204_1 \ldots 204_N$ is a continuous array of light detection elements, arranged in a radial pattern with respect to emitter 202 (analogous to emitter 102 of FIG. 2).

Processor 108 obtains data from reflectance detectors $104_1 \ldots 104_N$ or from transmittance detectors $124_1 \ldots 124_N$ through interface 110, and performs the necessary computations and data analysis. Interface 110 includes any relevant components for passing data from the detectors to processor 108, such as a driver, an amplifier, and an analog to digital converter. Processor 108 may send data to be displayed on display 112. Display may be, for example, a microdisplay unit embedded within device 100, or an output device (e.g., a monitor) associated with an external computer.

Controller 106 is an optional element, which may be used to adjust various parameters of the emitted light, such as the intensity, wavelength, duration, and the like. Operator interface 114 is an optional element, which enables the person implementing the disclosed technique (e.g. a physician, a medical aide, and the like) to select the relevant parameters of the emitted light, in accordance with relevant criteria (e.g., the type of the body part, the medical condition of the subject, and the like).

Body contact means 116 is optionally disposed on the region of body part 120 at which the light is emitted. Body contact means 116 is for example a fiber optic face plate, which serves as an optical interface between emitter 102 and detectors $104_1 \ldots 104_N$ on one side and body part 120 on the other side. Body contact means 116 directs light from emitter 102 toward body part 102 in a substantially perpendicular direction, and further directs the reflected light from body part 120 toward reflectance detectors $104_1 \ldots 104_N$. Body contact means 116 prevents any adverse crosstalk between emitter 102 and detectors $104_1 \ldots 104_N$. Body contact means 116 further functions as a protective layer, protecting the body part tissue from emitter 102 and detectors $104_1 \ldots 104_N$, as well as protecting emitter 102 and detectors $104_1 \ldots 104_N$ (especially their bonding wires) from possible damage due to friction with body part 120. Body contact means 116 may be integrated in the housing of sensor module 126.

Holding means 118 is an optional element, which enables the person implementing the disclosed technique to hold device 100 in a stable manner, and to accurately and effectively direct the emitted light onto body part 120. For example, holding means 118 may include a strap or adhesive material for attaching to the hand. Device 100 may optionally include a power supply (not shown), for powering the various components, for example via a battery or voltage mains. Device 100 may also optionally include a separate memory (not shown) for storing data.

According to one embodiment of the disclosed technique, operation, emitter 102 emits light (referenced 132 in FIG. 2) at the isosbestic wavelength toward body part 120. Since biological tissue is a turbid medium, which both scatters and absorbs light, some of the photons will be absorbed in the tissue and some will be scattered (either transmitted through or reflected back). The isosbestic wavelength is preferably approximately 803 nm (e.g., 803±5 nm). Other possible isosbestic wavelengths are: approximately 390 nm, approximately 422 nm, approximately 452 nm, approximately 500 nm, approximately 529 nm, approximately 545 nm, approximately 570 nm and approximately 584 nm.

A large portion of the emitted light is reflected diffusively toward the surface where the light is incident on the body part tissue, due to the high degree of scattering (biological tissue has low absorbance). Reflectance detectors $104_1 \ldots 104_N$ detect the diffuse reflectance (referenced 134 in FIG. 2), in accordance with a spatially resolved reflectance measurement technique. The absorption coefficient and the reduced scattering coefficient of the blood component of body part 120 (i.e., $\mu_a$ and $\mu_s'$) are then extracted from the spatially resolved reflectance measurements.

One technique for extracting the desired parameters employs a semi-analytic model, which relates the optical parameters of the tissue to the diffuse reflectance measurements. An example of such a model, as disclosed in Keinle et al., Applied Optics, Vol. 35, No. 13, pp. 2304-2314 (May, 1996), is as follows:

$$R(\rho) = \frac{a}{4\pi}\left[\frac{1}{\mu_t}\left(\mu_d + \frac{1}{r_1}\right)\frac{\exp(-\mu_d r_1)}{r_1^2} + \left(\frac{1}{\mu_t + 2z_b}\right)\left(\mu_d + \frac{1}{r_2}\right)\frac{\exp(-\mu_d r_2)}{r_2^2}\right]$$

where:

$$r_1 = \left[\left(\frac{1}{\mu_t}\right)^2 + \rho^2\right]^{1/2};$$

$$r_2 = \left[\left(\frac{1}{\mu_t} + 2z_b\right)^2 + \rho^2\right]^{1/2};$$

$$a = \frac{\mu_s'}{\mu_t};$$

-continued $$\mu_t = \mu_a + \mu'_s;$$

$$\mu_d = \sqrt{3\mu_a(\mu_a + \mu'_s)};$$

$z_b$=the distance from the tissue to an extrapolated boundary at which the fluence rate is forced to zero; and $\rho$=the radial distance from the point at which the light is incident on the tissue.

Theoretically, measuring $R(\rho)$ at two points is sufficient to extract the absorbance coefficient and the reduced scattering coefficient ($\mu_a$ and $\mu'_s$).

Another technique for extracting the desired parameters utilizes an experimental based calibration model. The calibration model is created using a large series of experimental observations of reflectance distributions for various optically well defined mediums, such as using polynomial regression. An example of such a calibration model is disclosed in Dam et al., Applied Optics, Vol. 40, No. 7, pp. 1155-1164 (March, 2001).

Processor 108 calculates the temporal derivatives from the extracted parameters based on a series of continuous measurements obtained by detectors $104_1 \ldots 104_N$. It is noted that device 100 may include any number of detectors $104_1 \ldots 104_N$ which are sufficient for obtaining spatially resolved reflectance measurements. Alternatively, device 100 may include a plurality of emitters and a single reflectance detector for implementing the spatially resolved reflectance measurements.

Figure 4:
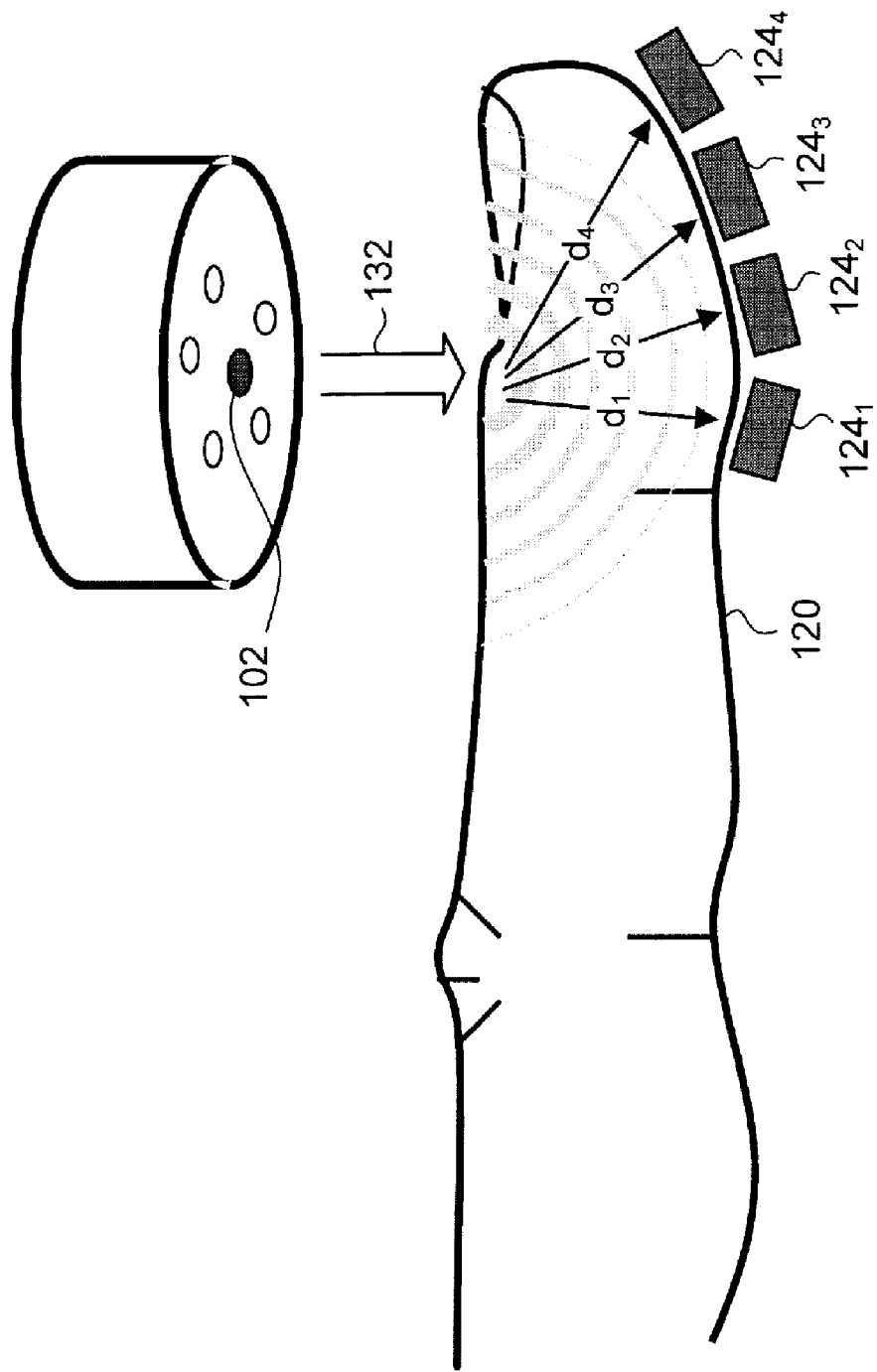
FIG. 4 is a schematic illustration of the device of FIG. 1 adapted for diffuse transmittance measurements, constructed an operative in accordance with a further embodiment of the disclosed technique.

According to another embodiment of the disclosed technique, the diffuse reflectance measurements are combined with diffuse transmittance measurements, to provide additional validation and increased accuracy. Reference is made to FIG. 4, which is a schematic illustration of the device of FIG. 1 adapted for diffuse transmittance measurements, constructed an operative in accordance with a further embodiment of the disclosed technique.

The Beer-Lambert law expresses the attenuation of light propagating through a uniformly absorbing medium. A modified form of the Beer-Lambert law can provide a more precise model for describing the total attenuation through biological tissue, by taking into account the significant contribution of the scattering phenomenon to the total attenuation, as follows:

$$T = \frac{I_{out}}{I_{in}} = F(\mu, d) \cdot e^{-\mu d} \quad (12)$$

where:
T=the transmittance through the medium;
$I_{out}$=the intensity of the light which passes through the medium;
$I_{in}$=the intensity of the incident light;
d=the distance that the light travels through the medium; and
$F(\mu,d)$=a complex function of $\mu_s$ and d.

Taking the logarithm of equation (12) and then differentiating with respect to d eliminates the complex function $F(\mu, d)$, resulting in:

$$\mu = \frac{\partial(\ln(I))}{\partial d} \quad (13)$$

Equation (13) yields the total attenuation through the medium.

Referring back to FIG. 3, transmittance detectors $124_1$, $122_2$, $122_3$ and $124_4$ are disposed opposite from the location of emitter 102 across body part 120 (e.g., if emitter 120 is positioned directly above body part 120, then detectors $124_1$, $124_2$, $124_3$, $124_4$ are positioned directly below body part 120 across from emitter 102). Detectors $124_1$, $124_2$, $124_3$, and $124_4$ are arranged at various distances (referenced $d_1$, $d_2$, $d_3$ and $d_4$, respectively), respective of emitter 102. Each of detectors $124_1$, $124_2$, $124_3$, $124_4$ detects the light passing through body part 120 along its respective distance. The distance derivative of equation (13) is then calculated (by processor 108) based on the measurements obtained by the detectors, to provide the total attenuation value ($\mu$). Subsequently, a simple iterative regression algorithm may be applied to extract the variables of $\mu_a$ and $\mu_s'$, by determining the values that provide an optimal fit (minimal deviation) for the reflectance measurements and the transmittance measurements. Other mathematical techniques known in the art may also be used to extract the desired coefficients based on the combination of the reflectance measurements and the transmittance measurements. Processor 108 then computes the temporal derivatives $$\left( \frac{\partial \mu_a}{\partial t} \text{ and } \frac{\partial \mu'_s}{\partial t} \right)$$

from these parameters. It is appreciated that four detectors are depicted in FIG. 3 for exemplary purposes only, and device 100 may use any number of detectors $124_N$ which are sufficient to detect the transmittance. Generally, a single transmittance detector is sufficient for obtaining diffuse transmittance measurements, and additional transmittance detectors may be utilized for validation of the measurement results. It is further appreciated that the reflectance measurements and transmittance measurements may be performed simultaneously (i.e., where reflectance detectors $104_1 \ldots 104_N$ carry out the spatially resolved reflectance measurements, and transmittance detectors $124_1 \ldots 124_N$ carry out the diffuse transmittance measurements).

The disclosed technique enables the measurement of hematocrit using only a single wavelength. This is advantageous, since emitting light at different wavelengths onto a living biological tissue may lead to various distortions in the subsequent analysis. Each wavelength may have a different penetration depth, resulting in inconsistent tissue volumes being inspected. Moreover, each wavelength may have a different dependency with respect to the various tissue components.

According to another embodiment of the disclosed technique, the hematocrit may be measured by emitting light at two separate wavelengths, rather than a single isosbestic wavelength. In this case, the absorbance of oxyhemoglobin and deoxyhemoglobin are not necessarily equal, and equation (3) cannot be reduced to equation (9). As a result, substituting equations (3) and (4) into equation (10) produces:

$$\frac{\frac{\partial \mu'_s}{\partial t}}{\frac{\partial \mu_a}{\partial t}} = \frac{\sigma_{scat}(1 - Hct)(1.4 - Hct)}{0.34(\sigma_{ox}SAT + (1 - SAT)\sigma_{deox}) + (1 - 0.34\,Hct)\mu_{a,plasma}} \quad (14)$$

Equation (14) contains two unknown variables: SAT=oxygen saturation level, and Hct=hematocrit value. This equation, or another relevant equation, can then be solved at two separate wavelengths (at least one of which is non-isosbestic) to determine both variables. For example, light may be emitted at approximately 690 nm and approximately 860 nm (preferably at two wavelengths where the absorbance spectra of oxyhemoglobin and deoxyhemoglobin are substantially far apart). Similarly, a third wavelength may be used, in order to provide additional validation to the measurement results.

According to a further embodiment of the disclosed technique, the hematocrit may be measured by emitting light at three separate wavelengths in the operational spectral range, by solving for three unknown variables in three separate equations. As stated earlier, in the operational spectral range the absorption of light is primarily due to the absorption due to the hemoglobin in the RBCs, and thus $\mu_{a,blood} \gg \mu_{a,plasma}$.

Accordingly, equation (3) becomes:

$$\mu_{a,blood} = \frac{0.34\,Hct}{V}(\sigma_{ox}SAT + (1-SAT)\sigma_{deox}) \qquad (15)$$

Substituting equation (15) into equation (7) results in:

$$\frac{\partial \mu_a}{\partial t} \cong \frac{0.34\,Hct}{V}\frac{\partial C_b}{\partial t}(\sigma_{ox}SAT + (1-SAT)\sigma_{deox}) \qquad (16)$$

Thus, the temporal variation of the absorption coefficient in the blood component is a function of three variables: the hematocrit value (Hct), the oxygen saturation level (SAT), and the temporal variation of the relative concentration of the blood $$\left(\frac{\partial C_b}{\partial t}\right).$$

Equation (15), or a similar relevant equation, can be solved at three different wavelengths within the operational spectral range, to determine these three unknown parameters. It is noted that the wavelength dependence of the absorption coefficient of the blood component ($\mu_{a,blood}$) is included in the absorption cross-section of the oxygenated and deoxygenated RBCs ($\sigma_{ox}$ and $\sigma_{deox}$), which are also wavelength dependent (and can be calculated using Mie theory, for example, as mentioned earlier). This approach also eliminates the use of the reduced scattering coefficient of the blood component ($\mu'_s$), which may be a less reliable measurement, in determining the hematocrit (or other parameters).

The disclosed technique allows continuous monitoring of the hematocrit value of the subject over a period of time, based on simple non-invasive optical measurements. This is particularly valuable for diagnosing or treating various medical conditions. One useful application of continuous hematocrit monitoring is for optimizing fluid status for a patient undergoing hemodialysis. Hemodialysis is a medical procedure, generally for treating patients suffering from kidney failure, in which waste products (e.g., ureic toxins and excess water in the blood plasma) are filtered out of the blood and the cleansed blood is restored to the body in a continuous circuit. The plasma refill rate of the patient is the rate at which the patient body transfers fluid back into the blood from the extravascular space, and the rate of dialysis filtration must be adapted with this rate. By continuously monitoring the hematocrit during the dialysis, the change in blood volume in the intravascular space can be detected, since the RBC count remains constant during dialysis and thus an increase in Hct indicates a reduction in plasma volume. The rate of dialysis filtration can then be set accordingly. A hemorrhaging patient who is receiving fluid or undergoing blood replacement can also be monitored in a similar manner. Hematocrit monitoring may also be used as part of other types of medical diagnostics and treatments, such as for anemia, dehydration, myeloproliferative disorders, chronic obstructive pulmonary disease, and other conditions. The hematocrit measurement may also be used as a test for determining suitability to donate blood or plasma.

Figure 5:
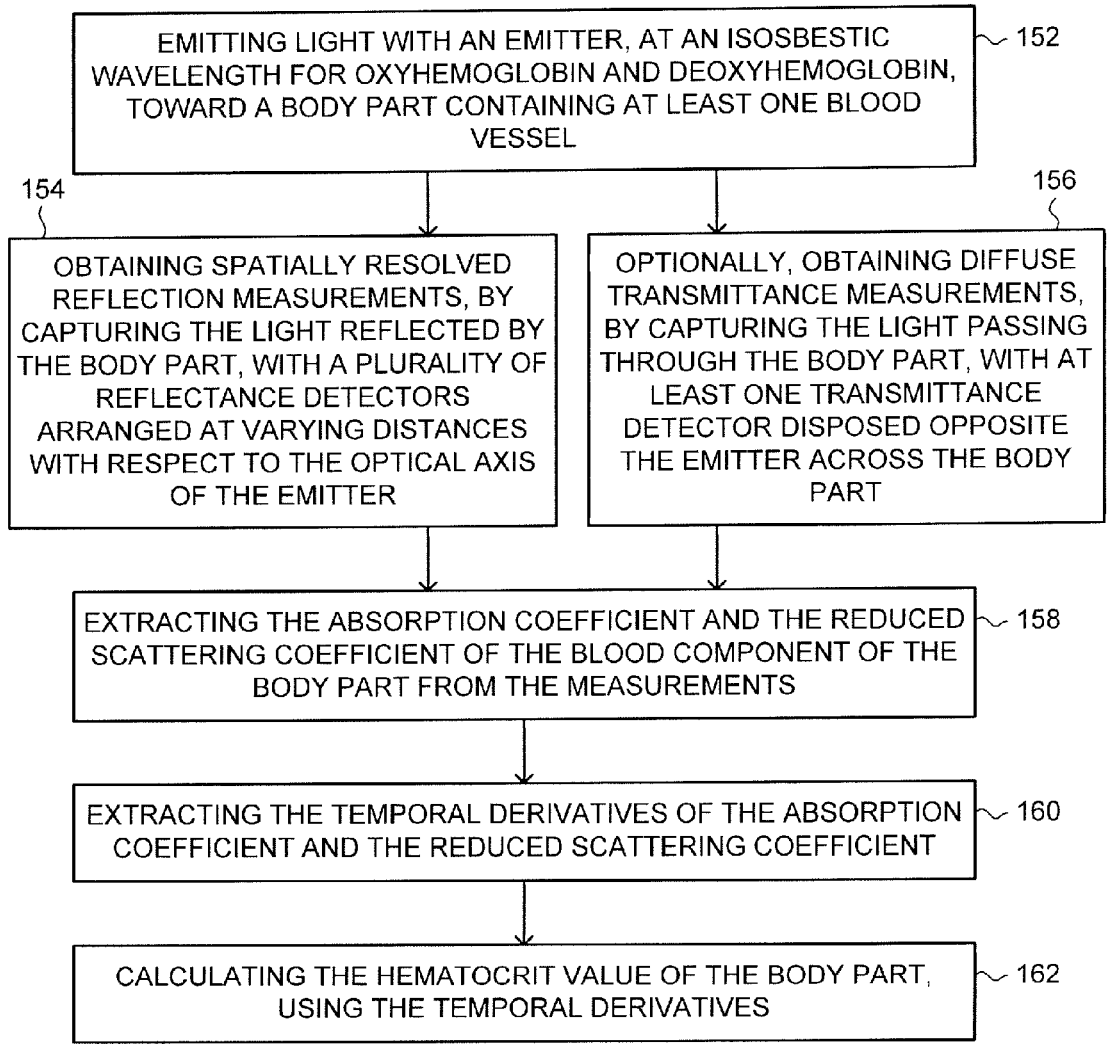
FIG. 5 is a schematic illustration of a method for monitoring the hematocrit of a subject, operative in accordance with an embodiment of the disclosed technique.

Reference is now made to FIG. 5, which is a schematic illustration of a method for monitoring the hematocrit of a subject, operative in accordance with an embodiment of the disclosed technique. In procedure 152, light is emitted from an emitter, at an isosbestic wavelength for oxyhemoglobin and deoxyhemoglobin, toward a body part containing at least one blood vessel. With reference to FIG. 2, emitter 102 emits light at an isosbestic wavelength (e.g., approximately 803 nm) toward body part 120.

In procedure 154, spatially resolved reflectance measurements are obtained, by capturing the light reflected by the body part, with a plurality of reflectance detectors arranged at varying distances with respect to the optical axis of the emitter. With reference to FIG. 2, reflectance detectors $104_1 \ldots 104_N$ are arranged at varying distances (e.g., in a radial pattern) with respect to the optical axis of emitter 102. Detectors $104_1 \ldots 104_N$ detect the light reflected from body part 120, obtaining a series of spatially resolved reflectance measurements.

In an optional procedure 156, diffuse transmittance measurements are obtained, by capturing the light passing through the body part, with at least one transmittance detector disposed opposite the emitter across the body part. With reference to FIG. 4, transmittance detectors $124_1$, $122_2$, $122_3$ and $124_4$ are disposed underneath body part 120 (i.e., opposite from the location of emitter 102 across body part 120), where each detector is positioned at a different distance (referenced $d_1$, $d_2$, $d_3$, $d_4$, respectively) with respect to the optical axis of emitter 102. Each of detectors $124_1$, $124_2$, $124_3$, $124_4$ detects the light passing through body part 120 along its respective distance, thereby obtaining a series of diffuse transmittance measurements. The total attenuation ($\mu$) through body part 120 is calculated based on the measurements.

In procedure 158, the absorption coefficient ($\mu_a$) and the reduced scattering coefficient ($\mu'_s$) of the blood component of the body part are extracted from the measurements. With reference to FIG. 1, processor 108 calculates the absorption coefficient and the reduced scattering coefficient of the blood component of body part 120 ($\mu_a$ and $\mu'_s$) from the spatially resolved reflectance measurements, and optionally, from the diffuse transmittance measurements as well. The parameters may be extracted using a semi-analytic model or using an experimentally based calibration model. An iterative regression algorithm may be used to combine the reflectance measurements and the transmittance measurements.

In procedure 160, the temporal derivatives of the absorption coefficient $$\left(\frac{\partial \mu_a}{\partial t}\right)$$

and the reduced scattering coefficient $$\left(\frac{\partial \mu'_s}{\partial t}\right)$$

of the blood component of the body part are extracted. With reference to FIG. 1, processor 108 calculates the temporal derivatives of the absorption coefficient and of the reduced scattering coefficient $$\left(\frac{\partial \mu_a}{\partial t} \text{ and } \frac{\partial \mu'_s}{\partial t}\right).$$

In procedure 162, the hematocrit value of the body part is calculated using the temporal derivatives. With reference to FIG. 1, processor 108 calculates the hematocrit based on the extracted temporal derivatives, by solving for the Hct variable in equation (11) or another similar relevant equation.

Figure 6:
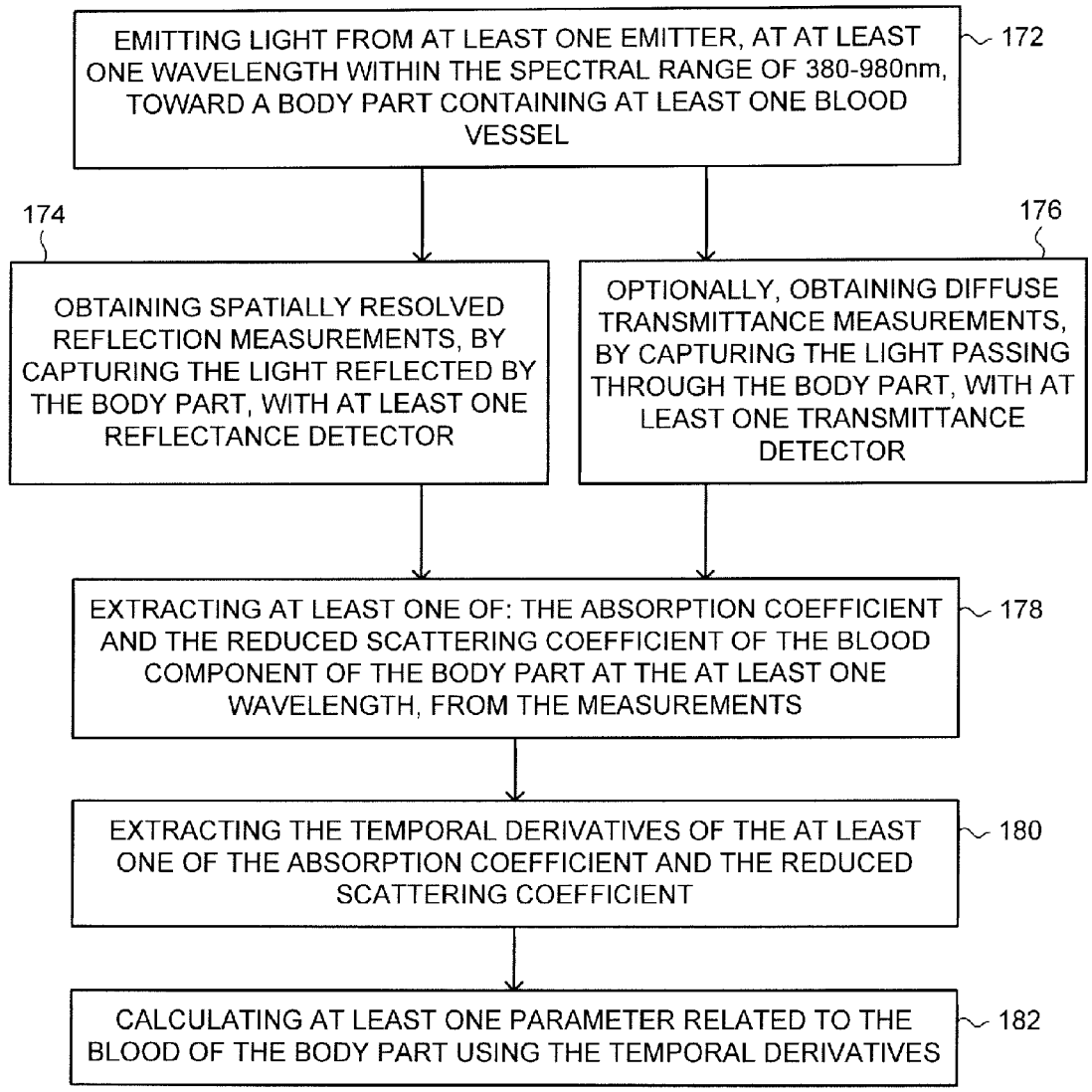
FIG. 6 is a schematic illustration of a method for measuring at least one parameter related to the blood of a subject, operative in accordance with another embodiment of the disclosed technique.

The disclosed technique is generally applicable to determining other blood parameters besides the hematocrit value, such as the oxygen saturation level, the hemoglobin concentration, the temporal variation of blood concentration $$\left(\frac{\partial C_b}{\partial t}\right),$$

the mean RBC size and size distribution, and the like. Reference is now made to FIG. 6, which is a schematic illustration of a method for measuring at least one parameter related to the blood of a subject, operative in accordance with another embodiment of the disclosed technique.

In procedure 172, light is emitted from at least one emitter, at least one wavelength within the spectral range of 380-980 nm, toward a body part containing at least one blood vessel. In procedure 174, spatially resolved reflectance measurements are obtained, by capturing the light reflected by the body part, with at least one reflectance detector. In an optional procedure 176, diffuse transmittance measurements are obtained, by capturing the light passing through the body part, with at least one transmittance detector.

In procedure 178, at least one of: the absorption coefficient ($\mu_a$) and the reduced scattering coefficient ($\mu'_s$) of the blood component of the body part at the at least one wavelength, is extracted from the measurements. In procedure 180, the temporal derivatives of the at least one of the absorption coefficient $$\left(\frac{\partial \mu_a}{\partial t}\right)$$

and the reduced scattering coefficient $$\left(\frac{\partial \mu'_s}{\partial t}\right)$$

of the blood component of the body part, is extracted. In procedure 182, at least one parameter related to the blood of the body part is calculated using the temporal derivatives.

It will be appreciated by persons skilled in the art that the disclosed technique is not limited to what has been particularly shown and described hereinabove.

The invention claimed is:

1. A method for measuring at least one parameter related to the blood of a subject, the method comprising the procedures of:
   emitting light with at least one emitter, at least one measurement wavelength within the spectral range of 380-980 nm, toward a body part containing at least one blood vessel;
   obtaining spatially resolved reflection measurements, by capturing light reflected by said body part, with at least one reflectance detector;
   extracting at least one of the adsorption coefficient ($\mu'_s$) and the reduced scattering coefficient ($\mu'_s$) of the blood component of said body part at each of said at least one wavelength, from said measurements;
   extracting the temporal derivatives of said at least one of said adsorption coefficient and said reduced scattering coefficient $$\left(\frac{\partial \mu'_s}{\partial t} \text{ and } \frac{\partial \mu_a}{\partial t}\right); \text{ and}$$

calculating said parameter using the ratio of said temporal derivatives at a single wavelength, for each of said at least one measurement wavelength.

2. The method of claim 1, wherein said parameter is the hematocrit value (Hct) of said subject.

3. The method of claim 2, wherein said procedure of emitting light comprises emitting light at an isosbestic wavelength for oxyhemoglobin and deoxyhemoglobin.

4. The method of claim 2, wherein said procedure of calculating comprises using said temporal derivatives in accordance with the following equation:

$$\frac{\sigma_{scat}(1 - Hct)(1.4 - Hct)}{\sigma_{abs}} = \frac{\frac{\partial \mu'_s}{\partial t}}{\frac{\partial \mu_a}{\partial t}}.$$

5. The method of claim 3, wherein said isosbestic wavelength is selected from the list consisting of:
   approximately 390 nm;
   approximately 422 nm;
   approximately 452 nm;
   approximately 500 nm;
   approximately 529 nm;
   approximately 545 nm;
   approximately 570 nm;
   approximately 584 nm; and
   approximately 803 nm.

6. The method of claim 1, further comprising the procedure of:
   obtaining diffuse transmittance measurements, by capturing light passing through said body part, with at least one transmittance detector disposed opposite said emitter across said body part.

7. The method of claim 1, wherein said body part is selected from the list consisting of:
   a finger;
   a toe;
   an outer ear;
   an eardrum;
   an earlobe;
   a mouth;
   an eye;
   a palm; and
   the webbing between fingers 8. The method of claim 1, wherein said parameter is selected from the list consisting of:
   oxygen saturation level;
   hemoglobin concentration;
   temporal variation of blood concentration;
   mean RBC size; and
   mean RBC size distribution.

9. The method of claim 1, wherein said procedure of emitting light comprises emitting light at least two measurement wavelengths, and said procedure of calculating comprises solving for the oxygen saturation level and hematocrit value of said subject, at each of said at least two measurement wavelengths.

10. The method of claim 9, wherein said procedure of calculating comprises using said temporal derivatives in accordance with the following equation:

$$\frac{\frac{\partial \mu'_s}{\partial t}}{\frac{\partial \mu_a}{\partial t}} = \frac{\sigma_{scat}(1-Hct)(1.4-Hct)}{0.34(\sigma_{ox}SAT + (1-SAT)\sigma_{deox}) + (1-0.34Hct)\mu_{a,plasma}} \ldots$$

11. The method of claim 1, wherein said procedure of emitting light comprises emitting light at least three measurement wavelengths, and said procedure of calculating comprises solving for the oxygen saturation level, the temporal variation of blood concentration, and hematocrit value of said subject, at each of said at least three measurement wavelengths.

12. The method of claim 11, wherein said procedure of calculating comprises using said temporal derivatives in accordance with the following equation:

$$\frac{\partial \mu_a}{\partial t} \cong \frac{0.34\,Hct}{V}\frac{\partial C_b}{\partial t}(\sigma_{ox}SAT + (1-SAT)\sigma_{deox}).$$

* * * * *